United States Patent
Nakazato et al.

(10) Patent No.: US 6,291,467 B1
(45) Date of Patent: Sep. 18, 2001

(54) HETEROAROMATIC DERIVATIVES

(75) Inventors: Atsuro Nakazato; Toshihito Kumagai; Shigeyuki Chaki; Kazuyuki Tomisawa, all of Tokyo; Masashi Nagamine, Osaka; Makoto Gotoh, Osaka; Masanori Yoshida, Osaka, all of (JP)

(73) Assignees: Taisho Pharmaceutical Co., Ltd.; Nihon Nohyaku Co. Ltd., both of (JP)

( * ) Notice: Subject to any disclaimer, the term of this patent is extended or adjusted under 35 U.S.C. 154(b) by 0 days.

(21) Appl. No.: 09/646,309

(22) PCT Filed: Mar. 18, 1998

(86) PCT No.: PCT/JP98/01163

§ 371 Date: Sep. 15, 2000

§ 102(e) Date: Sep. 15, 2000

(87) PCT Pub. No.: WO99/47513

PCT Pub. Date: Sep. 23, 1999

(51) Int. Cl.[7] ............ C07D 417/06; A61K 31/427; A61K 31/435; A61K 31/4188; A61P 25/15
(52) U.S. Cl. ............ 514/256; 514/274; 514/275; 514/326; 514/330; 514/335; 544/297; 544/298; 544/332; 546/209; 546/210; 546/211
(58) Field of Search ............ 546/210, 209, 546/211; 544/297, 298, 332, 330, 335; 514/326, 256, 275, 274

(56) References Cited

U.S. PATENT DOCUMENTS

| | | | |
|---|---|---|---|
| 5,059,601 | 10/1991 | Salimbeni et al. | 514/255 |
| 5,684,020 | 11/1997 | Peglion et al. | 514/320 |
| 5,693,655 | 12/1997 | Bottcher et al. | 514/323 |
| 5,714,498 | 2/1998 | Kulagowski et al. | 514/307 |

FOREIGN PATENT DOCUMENTS

| | | |
|---|---|---|
| 0-816-362 | 1/1998 | (EP) . |
| 2-240068 | 9/1990 | (JP) . |
| 4-352770 | 12/1992 | (JP) . |
| 7-291969 | 11/1995 | (JP) . |
| 8-508030 | 8/1996 | (JP) . |
| 8-325257 | 12/1996 | (JP) . |
| 10-095779 | 4/1998 | (JP) . |

*Primary Examiner*—Deborah C. Lambkin
*Assistant Examiner*—Andrea M D'Souza
(74) *Attorney, Agent, or Firm*—Manelli Denison & Selter PLLC; Paul E. White, Jr.

(57) ABSTRACT

An aromaheterocyclic derivative represented by the formula:

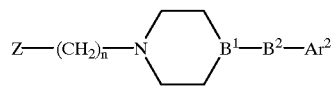

wherein Z is a group represented by the following formula:

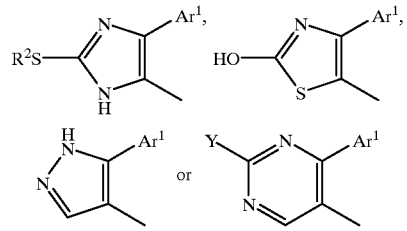

wherein $Ar^1$ is a phenyl group or a phenyl group substituted with a halogen atom or an alkyl group of 1 to 5 carbon atoms, $R^2$ is an alkyl group of 1 to 5 carbon atoms, Y is a hydrogen atom, a mercapto group, an alkylthio group of 1 to 5 carbon atoms, an amino group or an amino group substituted with one or two alkyl groups having 1 to 5 carbon atoms, $Ar^2$ is a phenyl group of one or two substituents selected from the group consisting of a halogen atom, an alkyl group of 1 to 5 carbon atoms, an alkoxy group of 1 to 5 carbon atoms, a hydroxyl group and a trifluoromethyl group, or a phenyl group, $B^1$–$B^2$ is CH—CO or C═C($R^1$) (wherein $R^1$ is a hydrogen atom or an alkyl group of 1 to 5 carbon atoms), and n is an integer of 1 to 4, or a pharmaceutically acceptable salt thereof, which is a dopamine $D_4$ receptor antagonist compound having an antipsychotic action without causing extrapyramidal diseases.

6 Claims, No Drawings

HETEROAROMATIC DERIVATIVES

TECHNICAL FIELD

The present invention relates to dopamine $D_4$ receptor antagonist compounds useful as antipsychotic drugs.

BACKGROUND ART

Antipsychotic agents are used not only for treating schizophrenia and problem behaviors associated with cerebrovascular diseases and senile dementia (e.g. aggressive behaviors, psychogenic excitement, ecdemomania or delirium). However, dopamine $D_2$ receptor antagonists, prior art antipsychotic drugs, cause serious extrapyramidal diseases as side effects, which has been a serious problem.

On the other hand, recently found dopamine $D_4$ receptors are similar to dopamine $D_2$ receptors in structure and properties, but are utterly different from dopamine $D_2$ receptors in intracerebral distributions. The intracerebral distribution of dopamine $D_4$ receptors is such that they are present in a high concentrations in the corticocerebral frontal lobe concerned with the onset of schizophrenia and are present in a low concentration in the striatum concerned with the onset of extrapyramidal diseases. Accordingly, unlike dopamines $D_2$ receptor antagonists, dopamine $D_4$ receptor antagonists are very likely to become novel therapeutic agents of schizophrenia without extrapyramidal diseases as side effects (Nature, 350, 610–614 (1991); Nature, 358, 109 (1992); Nature, 365, 393 (1993); Nature, 365, 441–445 (1993)).

Among such compounds is included clozapine. It has been reported that the affinity of clozapine for dopamine $D_4$ receptors is higher than that for dopamine $D_2$ receptors (Nature, 350, 610–614 (1991)). It has also been reported that in a clinical investigation of clozapine, unlike dopamine $D_2$ receptor, clozapine is effective on drug-resistant schizophrenia and negativism and hardly causes extrapyramidal diseases (Arch. Gen. Psych., 45, 789–796 (1988)). However, clozapine has a serious defect of causing blood disorder called agranulocytosis, and cases of death therefrom have been reported (Summary and Clinical Data, Sandoz, Canada Inc. (1990)).

Accordingly, dopamine $D_4$ receptor antagonists without such side-effects are very useful as therapeutic agents of schizophrenia which are very unlikely to cause extrapyramidal diseases.

An object of the present invention is to provide dopamine $D_4$ receptor antagonist compounds which have an antipsychotic action without causing extrapyramidal diseases.

DISCLOSURE OF THE INVENTION

As a result of extensive researches about aromaheterocyclic derivatives, the present inventors have found novel aromaheterocyclic derivatives having a high affinity for dopamine $D_4$ receptor, thus the present invention has been accomplished.

The present invention is explained as bellow:

The present invention is directed to an aromaheterocyclic derivative represented by Formula [I]:

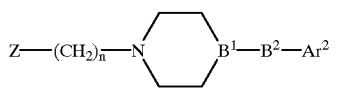

[I]

wherein Z is a group represented by the following Formula [II], [III], [IV] or [V]:

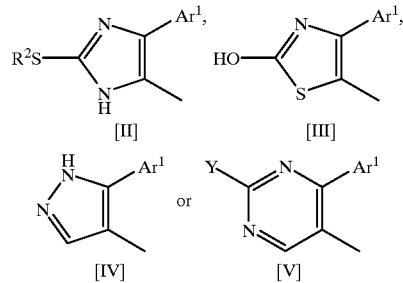

wherein $Ar^1$ is a phenyl group or a phenyl group substituted with a halogen atom or an alkyl group of 1 to 5 carbon atoms, $R^2$ is an alkyl group of 1 to 5 carbon atoms, Y is a hydrogen atom, a mercapto group, an alkylthio group of 1 to 5 carbon atoms, an amino group or an amino group substituted with one or two alkyl groups having 1 to 5 carbon atoms, $Ar^2$ is a phenyl group of one or two substituents selected from the group consisting of a halogen atom, an alkyl group of 1 to 5 carbon atoms, an alkoxy group of 1 to 5 carbon atoms, a hydroxyl group and a trifluoromethyl group, or a phenyl group, $B^1-B^2$ is CH—CO or C=C($R^1$) (wherein $R^1$ is a hydrogen atom or an alkyl group of 1 to 5 carbon atoms), and n is an integer of 1 to 4; or a pharmaceutically acceptable salt thereof.

In the present invention, the alkyl group of 1 to 5 carbon atoms refers to a straight or branched alkyl group, and examples thereof are a methyl group, an ethyl group, a propyl group, an isopropyl group, a butyl group and an isobutyl group. The alkylthio group of 1 to 5 carbon atoms refers to a straight or branched alkylthio group, and examples thereof are a methylthio group, an ethylthio group, a propylthio group, an isopropylthio group, a butylthio group and an isobutylthio group. The halogen atom refers to a fluorine atom, a chlorine atom, a bromine atom or an iodine atom. Accordingly, examples of the phenyl group of one or two substituents selected from the group consisting of a halogen atom, an alkyl group of 1 to 5 carbon atoms, an alkoxy group of 1 to 5 carbon atoms, a hydroxyl group and a trifluoromethyl group are a 2-fluorophenyl group, a 3-fluorophenyl group, a 4-fluorophenyl group, a 4-chlorophenyl group, a 4-bromophenyl group, a 3,4-dichlorophenyl group, a 4-methylphenyl group, a 3-trifluoromethylphenyl group, a 4-methoxyphenyl group, a 3,4-dimethoxyphenyl group and a 4-hydroxyphenyl group.

In addition, the pharmaceutically acceptable salt in the present invention includes salts with mineral acids such as sulfuric acid, hydrochloric acid or phosphoric acid, and salts with organic acids such as acetic acid, oxalic acid, lactic acid, tartaric acid, fumaric acid, maleic acid, trifluoroacetic acid or methanesulfonic acid.

Preferred compounds in the present invention can be indicated as follows:

That is, when Z is a group represented by Formula [II] or [III] in Formula [I], preferred compounds are those wherein $Ar^1$ is a fluorophenyl group, $Ar^2$ is a phenyl group substituted with a halogen atom, $B^1-B^2$ is CH—CO or C=CH and n is 2, and especially preferred compounds are those wherein $Ar^2$ is a fluorophenyl group and $B^1-B^2$ is C=CH. When Z is a group represented by Formula [IV] in Formula [I], preferred compounds are those wherein $Ar^1$ is a phenyl group or a phenyl group substituted with a fluorine atom or a methyl group, $Ar^2$ is a phenyl group substituted with a halogen atom or an alkyl group of 1 to 5 carbon atoms, $B^1-B^2$ is CH—CO or C=CH and n is 2, and especially preferred compounds are those wherein $Ar^2$ is a phenyl group substituted with a fluorine atom or a methyl group and $B^1-B^2$ is C=CH. When Z is a group represented by Formula [V] in Formula [I], preferred compounds are those wherein $Ar^1$ is a fluorophenyl group, $Ar^2$ is a phenyl group substituted with a halogen atom, Y is a hydrogen atom, a mercapto group or a methylthio group, $B^1-B^2$ is CH—CO or C=CH and n is 2, and especially preferred compounds are those wherein $Ar^2$ is a fluorophenyl group and $B^1-B^2$ is C=CH.

In the present specification, a imidazolyl ring or a pyrazolyl ring is, for the sake of convenience, indicated by one of the tautomers thereof, but both are included within the scope of the present invention.

The compound of Formula [I] can be prepared by the following methods. In the following reaction formulae, $Ar^1$, $Ar^2$, $R^1$, $R^2$, $B^1-B^2$ and n are as defined above, $R^3$ is an alkyl group of 1 to 5 carbon atoms, $R^4$ and $R^5$ are each a methyl group, or $R^4$ and $R^5$ taken together with the nitrogen atom to which they are attached form a pyrrolidino group, a piperidino group, a morpholino group or an N-methylpiperazino group, $R^6$ is a protecting group of the nitrogen atom such as, for example, an alkoxycarbonyl group (e.g. a t-butoxycarbonyl group or an ethoxycarbonyl group), an acyl group (e.g. an acetyl group or a benzoyl group), a sulfonyl group (e.g. a tosyl group), an alkyl group of 1 to 5 carbon atoms or a benzyl group, $R^7$ is an alkyl group of 1 to 5 carbon atoms, M is, for example, a sodium atom, a potassium atom or $NH_4$, $X^1$ is a chlorine atom, a bromine atom or an iodine atom, $X^2$ is an inorganic acid (e.g. HCl, HBr, HI or $1/2H_2SO_4$), and Y is an alkyl group of 1 to 5 carbon atoms, an alkylthio group of 1 to 5 carbon atoms or an amino group.

<Preparation Method 1>

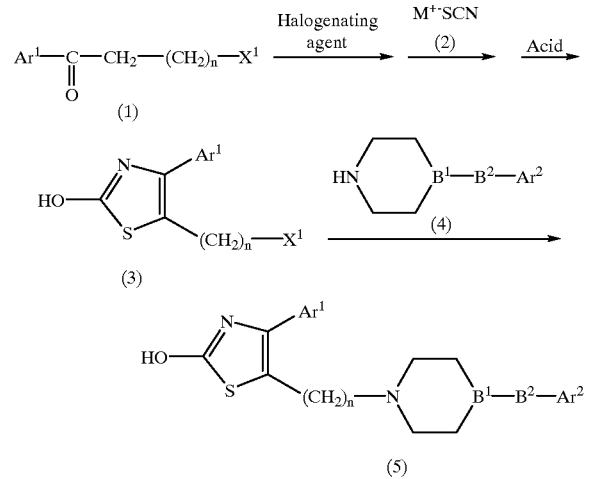

A ketone derivative (1) is halogenated with a halogenating agent in an inert solvent, and reacted with a thiocyanate (2) in an inert solvent, followed by an acid treatment to give 2-hydroxythiazole derivative (3).

The inert solvent includes organic carboxylic acids (e.g. acetic acid), organic halogenides (e.g. carbon tetrachloride or chloroform), alcohols (e.g. ethanol or isopropanol), ethers (e.g. diethyl ether or tetrahydrofuran), hydrocarbons (e.g. toluene), N,N-dimethylformamide, acetonitrile, water or a mixture thereof. Examples of the halogenating agent are chlorine, bromine, iodine, N-chlorosuccinimide, N-bromosuccinimide and sulfuryl chloride. The acid treatment refers to a reaction with an acid such as hydrochloric acid, sulfuric acid, acetic acid, trifluoroacetic acid, methansulfonic acid, tosylic acid or a mixture thereof in an alcohol (e.g. methanol or ethanol), an ether (e.g. dioxane), acetone or water.

Subsequently, the 2-hydroxythiazole derivative (3) is reacted with an amine (4) in the presence or absence of a base in an inert solvent to give a compound (5) of the present invention.

Examples of the base are organic amines (e.g. triethylamine, N,N-diisopropylethylamine or pyridine), alcoholates (e.g. sodium ethoxide), alkali metal amides (e.g. sodium amide), inorganic bases (e.g. sodium bicarbonate, sodium carbonate, potassium carbonate, sodium hydroxide or sodium hydride). Examples of the inert solvent are organic halogenides (e.g. carbon tetrachloride or chloroform), alcohols (e.g. methanol, ethanol or isopropanol), ethers (e.g. diethyl ether or tetrahydrofuran), hydrocarbons (e.g. toluene), N,N-dimethylformamide, acetonitrile, water and a mixture thereof.

The amine (4) can be prepared according to the method described below.

<Preparation method 2>

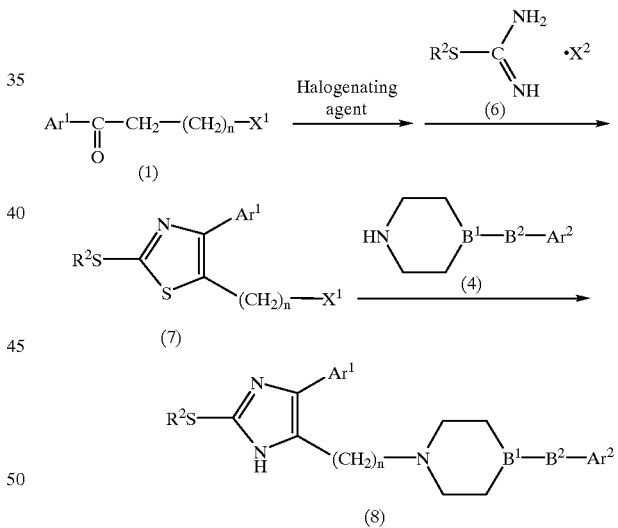

The compound (1) is halogenated according to the same method as in the first step of Preparation Method 1, reacted with a S-alkylisothiourea (6) in the presence of a base in an inert solvent to give an imidazole derivative (7).

Examples of the base are organic amines (e.g. triethylamine, N,N-diisopropylethylamine or pyridine), alcoholates (e.g. sodium ethoxide), alkali metal amides (e.g. sodium amide), organic carboxylic acid alkali metal salts (e.g. sodium acetate), inorganic bases (e.g. sodium bicarbonate, sodium carbonate, potassium carbonate, sodium hydroxide or sodium hydride). Examples of the inert solvent are organic carboxylic acids (e.g. acetic acid), organic halogenides (e.g. carbon tetrachloride or chloroform), alcohols (e.g. methanol or isopropanol), ethers (e.g. diethyl ether or tetrahydrofuran), hydrocarbons (e.g. toluene), N,N-dimethylformamide, acetonitrile, water and a mixture thereof.

Then, the imidazole derivative (7) is reacted with an amine (4) in the presence or absence of a base in an inert solvent to give a compound (8) of the present invention.

Examples of the base are organic amines (e.g. triethylamine, N,N-diisopropylethylamine or pyridine), alcoholates (e.g. sodium ethoxide), alkali metal amides (e.g. sodium amide), organic carboxylic acid alkali metal salts (e.g. sodium acetate), inorganic bases (e.g. sodium bicarbonate, sodium carbonate, potassium carbonate, sodium hydroxide or sodium hydride). Examples of the inert solvent are organic carboxylic acids (e.g. acetic acid), organic halogenides (e.g. carbon tetrachloride or chloroform), alcohols (e.g. methanol, ethanol or isopropanol), ethers (e.g. diethyl ether or tetrahydrofuran), hydrocarbons (e.g. toluene), N,N-dimethylformamide, acetonitrile, water and a mixture thereof.

<Preparation Method 3>

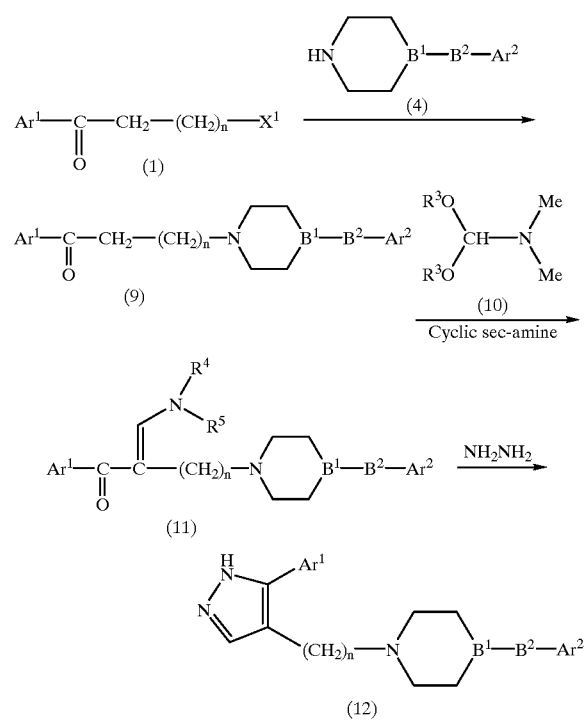

The ketone derivative (1) is reacted with the amine (4) in the presence or absence of a base in an inert solvent or without solvent to give an aminoketone derivative (9).

Examples of the base are tertiary amines (e.g. triethylamine or N,N-diisopropylethylamine), inorganic bases (e.g. potassium carbonate, sodium carbonate, potassium bicarbonate, sodium bicarbonate, potassium hydroxide, sodium hydroxide or sodium hydride). Examples of the inert solvent are organic carboxylic acids (e.g. acetic acid), organic halogenides (e.g. carbon tetrachloride or chloroform), alcohols (e.g. methanol, ethanol or isopropanol), ethers (e.g. diethyl ether or tetrahydrofuran), hydrocarbons (e.g. toluene), N,N-dimethylformamide, acetonitrile, water and a mixture thereof.

Then, the aminoketone derivative (9) is reacted with an N,N-dimethylformamide dialkylacetal (10) in the presence or absence of a cyclic amine in an inert solvent to give an enamine derivative (11), which is then reacted with hydrazine to give a compound (12) of the present invention.

The cyclic amine includes pyrrolidine, piperidine, morpholine, N-methylpiperazine and the like. Examples of the inert solvent are ethers (e.g. tetrahydrofuran or dioxane), hydrocarbons (e.g. benzene or toluene), acetonitrile and N,N-dimethylformamide. The solvent in the reaction with hydrazine includes alcohols (e.g. methanol, ethanol or isopropanol), ethers (e.g. diethyl ether or tetrahydrofuran), hydrocarbons (e.g. toluene), N,N-dimethylformamide, acetonitrile, water, a mixture thereof and the like.

Furthermore, the aminoketone derivative (9) is formylated according to an ordinary formylation of an activated methylene group using a formic acid ester and a base, followed by the same reaction as described above using hydrazine to give a compound (12) of the present invention.

<Preparation Method 4>

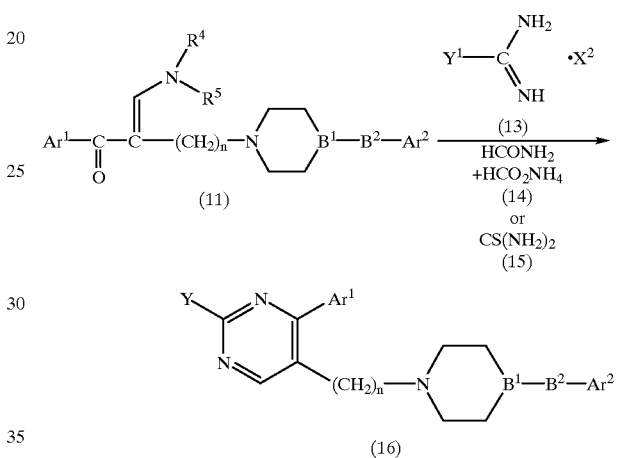

The enamine derivative (11) is reacted with a mixture (14) of formamide and ammonium formate, a compound represented by Formula (13), or thiourea (15), if necessary, in the presence or absence of a base in an inert solvent to give a compound (16) of the present invention.

Examples of the base are tertiary amines (e.g. triethylamine or N,N-diisopropylethylamine), organic carboxylic acid alkali metal salts (e.g. sodium acetate), inorganic bases (e.g. potassium carbonate, sodium carbonate, potassium bicarbonate, sodium bicarbonate, potassium hydroxide, sodium hydroxide or sodium hydride). Examples of the inert solvent are organic carboxylic acids (e.g. acetic acid), organic halogenides (e.g. carbon tetrachloride or chloroform), alcohols (e.g. methanol, ethanol or isopropanol), ethers (e.g. diethyl ether or tetrahydrofuran), hydrocarbons (e.g. toluene), N,N-dimethylformamide, acetonitrile, water and a mixture thereof.

<Preparation Method 5>

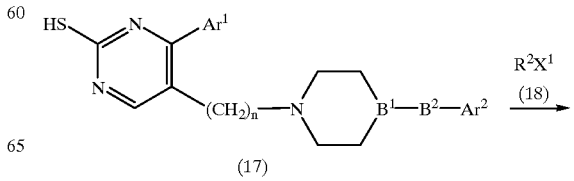

-continued

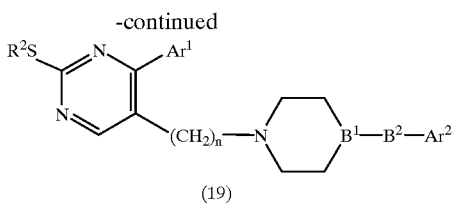

The mercapto derivative (17) (Y=HS in Formula (16)) obtained according to Preparation Method 4 is reacted with an alkyl halide (18) in the presence or absence of a base in an inert solvent to give a compound (19) of the present invention.

Examples of the base are tertiary amines (e.g. triethylamine or N,N-diisopropylethylamine), organic carboxylic acid alkali metal salts (e.g. sodium acetate), inorganic bases (e.g. potassium carbonate, sodium carbonate, potassium bicarbonate, sodium bicarbonate, potassium hydroxide, sodium hydroxide or sodium hydride). Examples of the inert solvent are organic carboxylic acids (e.g. acetic acid), organic halogenides (e.g. carbon tetrachloride or chloroform), alcohols (e.g. methanol, ethanol or isopropanol), ethers (e.g. diethyl ether or tetrahydrofuran), hydrocarbons (e.g. toluene), N,N-dimethylformamide, acetonitrile, water and a mixture thereof.

<Preparation Method 6>

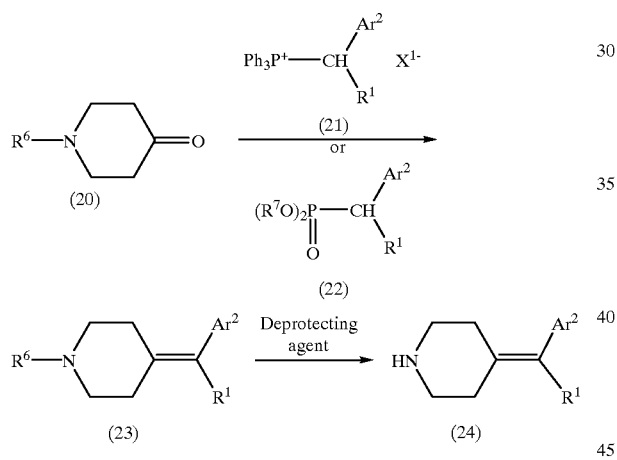

A 4-benzylidenepiperidine compound (24) can be prepared by condensing a piperidone derivative (20) with a triphenylarylmethyl phosphonium salt (21) or a dialkylarylmethyl phosphonate (22) in the presence of a base in an inert solvent, and then removing the protective group with deprotecting agent.

Examples of the base are sodium hydride, potassium hydride, sodium methoxide, potassium t-butoxide, n-butyl lithium, lithium diisopropylamide, lithium bis (trimethylsilyl)amide and sodium amide, and if necessary, they can be used together with a catalyst (e.g. 15-crown-5 ether or 18-crown-6 ether), tetramethylethylenediamine or hexamethylphosphoramide. Examples of the inert solvent are ethers (e.g. diethyl ether, tetrahydrofuran or dioxane), hydrocarbons (e.g. benzene or toluene), alcohols (e.g. ethanol), N,N-dimethylformamide, dimethylsulfoxide, water and a mixture thereof. Examples of a reaction solvent to be used for the deprotection are ethers (e.g. diethyl ether, tetrahydrofuran or dioxane), hydrocarbons (e.g. benzene or toluene), alcohols (e.g. ethanol), organic carboxylates (e.g. ethyl acetate), ketones (e.g. acetone), halogenated alkanes (dichloromethane or chloroform), organic carboxylic acids (e.g. acetic acid), N,N-dimethylformamide and water. Examples of the deprotecting agent, in case where $R^6$ is an alkoxycarbonyl group, an acyl group or a sulfonyl group, are acids such as inorganic acids (e.g. hydrochloric acid, hydrobromic acid or sulfuric acid), organic acids (e.g. trifluoroacetic acid, formic acid or methanesulfonic acid) or a solution of hydrogen chloride in dioxane or ethyl acetate, and bases such as inorganic bases (e.g. sodium hydroxide, potassium hydroxide or barium hydroxide). In case where $R^6$ is an alkyl group of 1 to 5 carbon atoms or a benzyl group, after conversion into an alkoxycarbonyl group according to a reaction with an alkyl haloformate (e.g. ethyl chloroformate) in the presence or absence of a base, deprotection is carried out in the same manner as described above. In case where $R^6$ is a benzyl group, deprotection can be carried out according to a Birch reduction.

The compounds of the present invention show a superior affinity for dopamine $D_4$ receptor but does not show a low affinity for dopamine $D_2$ receptor, and have a superior selectivity. Accordingly, the compounds of the present invention are useful for the prevention or treatment of problem behaviors associated with cerebrovascular diseases and senile dementia, and useful as drugs without extrapyramidal diseases as side-effects.

For the above-mentioned purposes, the compounds of the present invention are combined with conventional fillers, binding agents, disintegrators, pH modulators, solbilizers, etc. to formulate into tablets, pills, granules, powders, solutions, emulsions, suspensions, injections, etc. according to conventional preparation techniques.

The compound of the present invention can be administered orally or parenterally in the dose of from 0.1 to 500 mg/day to an adult patient in a single portion or several divided portions. This dose can be properly increased or decreased on the type of diseases, the age, body weight or symptoms of the patient.

BEST MODE OF CARRYING OUT THE INVENTION

The present invention is illustrated in more detail by showing the following examples and experiments.

EXAMPLE 1

Synthesis of 2-hydroxy-5-(2-chloroethyl)-4-(4-fluorophenyl)thiazole

To a solution of 20.08 g of 4-chloro-4'-fluorobutyrophenone in 80 ml of chloroform was added dropwise a solution of 5.2 ml of bromine in 10 ml of chloroform over 30 minutes. The reaction mixture was stirred at room temperature for an hour, and concentrated under reduced pressure.

The residue was dissolved in 120 ml of ethanol, and 9.80 g of potassium thiocyanate was added, followed by reflux with heating with stirring for an hour. The reaction solution was concentrated under reduced pressure, and to the residue was added water, followed by extracting with ethyl acetate. The extract was washed with water and a saturated aqueous sodium chloride solution, dried over anhydrous sodium sulfate, and the drying agent was removed by filtration, followed by concentration under reduced pressure.

The residue was refluxed in a mixture of 140 ml of acetic acid, 40 ml of water and 15 ml of sulfuric acid with heating with stirring for 3 hours. The reaction solution was concentrated under reduced pressure, and the residue was poured into ice water and extracted with ethyl acetate. The extract was washed with water, a saturated aqueous sodium bicarbonate solution and a saturated aqueous sodium chloride solution and dried over anhydrous sodium sulfate, and after removal of the drying agent by filtration, the filtrate was concentrated under reduced pressure. The residue was crystallized by addition of isopropyl ether, and recrystallized from hexane-ethyl acetate to give 16.40 g of 2-hydroxy-5-(2-chloroethyl)-4-(4-fluorophenyl)thiazole.

m.p. 140.0–141.5° C.

Example 2

Synthesis of 2-methylthio-5-(2-chloroethyl)-4-(4-fluorophenyl)imidazole (2-methylthio-4-(2-chloroethyl)-5-(4-fluorophenyl)imidazole)

To a solution of 2.00 g of 4-chloro-4'-fluorobutyrophenone in 5 ml of chloroform was added dropwise a solution of 0.52 ml of bromine in 1 ml of chloroform over 5 minutes. The reaction mixture was stirred at room temperature for an hour, and concentrated under reduced pressure.

The residue was dissolved in 20 ml of N,N-dimethylformamide, and then 3.50 g of S-methylisothiourea hydrochloride, 2.76 g of anhydrous potassium carbonate and 0.15 g of sodium iodide were added, followed by stirring with heating at 80° C. for an hour. The reaction solution was poured into ice water, and extracted with diethyl ether. The extract was washed with water and a saturated aqueous sodium chloride solution and dried over anhydrous sodium sulfate. The drying agent was removed by filtration, followed by concentration under reduced pressure. The residue was purified by a flash column chromatography (silica gel: Wakogel C200 (manufactured by Wako Pure Chemicals), eluent; hexane-ethyl acetate=2:1) and recrystallized from isopropyl ether to give 1.13 g of 2-methylthio-5-(2-chloroethyl)-4-(4-fluorophenyl)imidazole (2-methylthio-4-(2-chloroethyl)-5-(4-fluorophenyl)-imidazole).

m.p. 134.0–135.0° C.

EXAMPLE 3

Synthesis of 2-hydroxy-4-(4-fluorophenyl)-5-[2-[4-(3-fluorobenzylidene)piperidin-1-yl]ethyl]thiazole In 2 ml of methanol were stirred 773 mg of 2-hydroxy-5-(2-chloroethyl)-4-(4-fluorophenyl)thiazole, 683 mg of 4-(3-fluorobenzylidene)piperidine hydrochloride and 1.04 ml of N,N-diisopropylethylamine at 80° C. for 3 days. The reaction solution was concentrated under reduced pressure, and the residue was separated with ethyl acetate and a saturated aqueous sodium bicarbonate solution. The organic layer was washed with a saturated aqueous sodium chloride solution and dried over anhydrous sodium sulfate, and the drying agent was removed by filtration. The filtrate was concentrated under reduced pressure, and the residue was purified by a flash column chromatography (silica gel; ChromatorexNH NHDM1020 (manufactured by Fuji-Davison Chemical Co.), eluent; hexane-ethyl acetate =1:1), and recrystallized from hexane-ethyl acetate to give 265 mg of 2-hydroxy-4-(4-fluorophenyl)-5-[2-[4-(3-fluorobenzylidene)piperidin-1-yl]ethyl]thiazole.

m.p. 140.5–142.0° C.

The structures and physical property data of the present compound and the compounds prepared in the same manner as in Example 3 are shown in Table 1.

EXAMPLE 4

Synthesis of 5-(4-fluorophenyl)-4-[2-[4-(2-fluorobenzylidene)piperidin-1-yl]ethyl]pyrazole oxalate (3 -(4-fluorophenyl)-4-[2-[4-(2-fluorobenzylidene)piperidin-1-yl]ethyl]pyrazole oxalate)

(1) In 10 ml of methanol were reacted 12.2 g of 2-(4-fluorophenyl)-2-(3-chloropropyl)-1,3-dioxolane, 11.4 g of 4-(2-fluorobenzylidene)piperidine hydrochloride and 19.4 g of N,N-diisopropylethylamine at 80° C. for 3 days. The reaction solution was separated with ethyl acetate and a saturated aqueous sodium bicarbonate solution, and the organic layer was dried over anhydrous sodium sulfate, followed by removal of the drying agent was by filtration. The filtrate was concentrated under reduced pressure and purified by a flash column chromatography (silica gel: Wakogel C200 (manufactured by Wako Pure Chemicals), eluent; hexane-ethyl acetate =3:1–1:1) to give 16.3 g of an oily compound.

This was stirred in a mixture of 75 ml of 1 N hydrochloric acid and 75 ml of tetrahydrofuran at room temperature for 16 hours. The reaction solution was concentrated under reduced pressure, the residue was separated with ethyl acetate and an aqueous 2N hydrochloric acid solution, and the organic layer was washed with a saturated aqueous sodium chloride solution. The organic layer was dried over anhydrous sodium sulfate, followed by removal of the drying agent was by filtration. The filtrate was concentrated under reduced pressure, treated with 4 N hydrogen chloride/1,4-dioxane solution and crystallized form ethyl acetate to give 12.9 g of 1-[4-(4-fluorophenyl)-4-oxobutyl]-4-(2-fluorobenzylidene)piperidine hydrochloride.

(2) A mixture of 1.96 g of 1-[4-(4-fluorophenyl)-4-oxobutyl]-4-(2-fluorobenzylidene)piperidine hydrochloride, 345 mg of anhydrous potassium carbonate, 5.0 ml of N,N-dimethylformamide dimethylacetal, 3.5 ml of pyrrolidine and 5.0 ml of N,N-dimethylformamide was stirred on an oil bath at 120° C. for 2.5 hours. The reaction solution was separated with ethyl acetate and water, and the organic layer was concentrated under reduced pressure to give a crude 1-[4-(4-fluorophenyl)-4-oxo-3-pyrrolidinomethylenebutyl]-4-(2-fluorobenzylidene)piperidine as an oil.

This was dissolved in 20 ml of methanol, and 3 ml of 80% aqueous hydrazine solution was added, followed by reflux with heating for 2 hours. The reaction solution was separated with a saturated aqueous sodium bicarbonate solution and ethyl acetate, and the organic layer was dried over anhydrous sodium sulfate, followed by removal of the drying agent by filtration. The filtrate was concentrated under reduced pressure, and the resulting residue was purified by a flash column chromatography (silica gel; ChromatorexNH NHDM1020 (manufactured by Fuji-Davison Chemical Co.), eluent; hexane-ethyl acetate =5:1–1:1) to give about 1.6 g of an oily compound, which was then dissolved in 15 ml of isopropanol, and a solution of 700 mg of oxalic acid in 10 ml of isopropanol was added. The precipitated crystals were collected by filtration and washed with a little amount of isopropanol to give 1.42 g of 3-(4-fluorophenyl)-4-[2-[4-(2-fluorobenzylidene)piperidin-1-yl]ethyl]pyrazole oxalate {3-(4-fluorophenyl)-4-[2-[4-(2-fluorobenzylidene)piperidin-1-yl]ethyl]pyrazole oxalate}.

m.p. 144.5–145.5° C.

The structures and physical property data of the present compound and the compounds prepared in the same manner as in Example 4 are shown in Table 1.

EXAMPLE 5

Synthesis of 4-(4-fluorophenyl)-5-[2-[4-(2-fluorobenzylidene)piperidin-1-yl]ethyl]pyrimidine dihydrochloride 6.04 g of 1-[4-(4-fluorophenyl)-4-oxobutyl]-4-(2-fluorobenzylidene)piperidine hydrochloride was separated with ethyl acetate and a saturated aqueous sodium bicarbonate solution, and the organic layer was dried over anhydrous sodium sulfate, followed by removal of the drying agent by filtration. The organic layer was concentrated under reduced pressure, and the resulting oily compound, 20.0 ml of N,N-dimethylformamide dimethylacetal, 14.0 ml of pyrrolidine and 12 ml of N,N-dimethylformamide were stirred on an oil bath at 120° C. for 2.5 hours. The reaction solution was concentrated under reduced pressure, and the residue was separated with ethyl acetate and water. The organic layer was washed with a saturated aqueous sodium chloride solution and dried over anhydrous sodium sulfate, followed by removal of the drying agent by filtration. The organic layer was concentrated under reduced pressure to give 7.16 g of a crude 1-[4-(4-fluorophenyl)-4-oxo-3-pyrrolidinomethylenebutyl]-4-(2-fluorobenzylidene) piperidine as an oil.

To 3.0 g of the crude 1-[4-(4-fluorophenyl)-4-oxo-3-pyrrolidinomethylenebutyl]-4-(2-fluorobenzylidene) piperidine were added 30 g of formamide, 3.0 g of ammonium formate and 0.6 ml of water, followed by stirring at 180° C. for 1.5 hours. The reaction solution was separated with ethyl acetate and a saturated aqueous sodium bicarbonate solution, and the organic layer was washed with a saturated aqueous sodium chloride solution and dried over anhydrous sodium sulfate, followed by removal of the drying agent by filtration. The filtrate was concentrated under reduced pressure, and the residue was purified by a flash column chromatography (silica gel; ChromatorexNH NHDM1020 (manufactured by Fuji-Davison Chemical Co.), eluent; hexane-ethyl acetate =6:1–4:1), treated with 4 N hydrogen chloride/1,4-dioxane solution and recrystallized form methanol-isopropyl ether to give 580 mg of 4-(4-fluorophenyl)-5-[2-[4-(2-fluorobenzylidene)piperidin-1-yl]ethyl]pyrimidine dihydrochloride.

m.p. 144.5–146.5° C.

The structures and physical property data of the present compound and the compounds prepared in the same manner as in Example 5 are shown in Table 1.

EXAMPLE 6

Synthesis of 4-(4-fluorophenyl)-5-[2-[4-(2-fluorobenzylidene)piperidin-1-yl]ethyl]-2-mercaptopyrimidine To 3.70 g of the crude 1-[4-(4-fluorophenyl)-4-oxo-3-pyrrolidinomethylenebutyl]-4-(2-fluorobenzylidene) piperidine obtained in Example 5 were added a solution of 0.45 g of potassium hydroxide in 40 ml of ethanol and 1.23 g of thiourea, followed by reflux with heating with stirring for 5 hours. The reaction solution was concentrated under reduced pressure, and to the residue were added a saturated aqueous ammonium chloride solution and a little amount of ethyl acetate. The precipitated crystals were collected by filtration, and recrystallized from ethyl acetate to give 1.27 g of 4-(4-fluorophenyl)-5-[2-[4-(2-fluorobenzylidene) piperidin-1-yl]ethyl]-2-mercaptopyrimidine.

m.p. 157.0–158.0° C.

The structures and physical property data of the present compound and the compounds prepared in the same manner as in Example 6 are shown in Table 1.

EXAMPLE 7

Synthesis of 4-(4-fluorophenyl)-5-[2-[4-(2-fluorobenzylidene)piperidin-1-yl]ethyl]-2-methylthiopyrimidine dihydrochloride To a solution of 284 mg of 4-(4-fluorophenyl)-5-[2-[4-(2-fluorobenzylidene)piperidin-1-yl]ethyl]-2-mercaptopyrimidine in 3 ml of N,N-dimethylformamide was added 42 µl of methyl iodide, followed by stirring at room temperature for 30 minutes. The reaction solution was poured into a saturated aqueous sodium bicarbonate solution and extracted with ethyl acetate. The extract was washed with water and a saturated aqueous sodium chloride solution and dried over anhydrous sodium sulfate, followed by removal of the drying agent by filtration. The filtrate was concentrated under reduced pressure, and the residue was purified by a flash column chromatography (silica gel; ChromatorexNH NHDM1020 (manufactured by Fuji-Davison Chemical Co.), eluent; hexane-ethyl acetate =10:1–8:1), treated with 4 N hydrogen chloride/1,4-dioxane solution and crystallized form isopropyl ether to give 310 mg of 4-(4-fluorophenyl)-5-[2-[4-(2-fluorobenzylidene) piperidin-1-yl]ethyl]-2-methylthiopyrimidine dihydrochloride.

H$^1$-NMR (CDCl$_3$) δ(ppm);

2.54(3H, s), 2.52–3.61(12H, m), 5.55(1H, br, s), 6.40(1H, s), 7.15–7.43(6H, m), 7.63–7.78(2H, m), 8.70(1H, s), 11.18 (1H, br, s)

MS m/e; 438 (M$^+$+1,100%)

The structures and physical property data of the present compound and the compounds prepared in the same manner as in Example 7 are shown in Table 1.

EXAMPLE 8

Synthesis of 4-(4-fluorobenzylidene)piperidine hydrochloride

To a stirred suspension of 13.20 g of 60% sodium hydride (in oil) containing 1.65 g of 15-crown-5 ether in 650 ml of tetrahydrofuran were added dropwise a solution of 59.78 g of N-t-butoxycarbonylpiperidone and 81.25 g of diethyl 4-fluorobenzylphosphonate in 150 ml of tetrahydrofuran under ice-cooling over 20 minutes. After stirring at room temperature for a day, a saturated aqueous sodium bicarbonate solution was added cautiously, followed by extracting with ethyl acetate. The extract was washed with a saturated aqueous sodium bicarbonate solution and a saturated aqueous sodium chloride solution, successively, and dried over anhydrous sodium sulfate, followed by removal of the drying agent by filtration. The filtrate was concentrated under reduced pressure and purified by a flash column chromatography (silica gel: Wakogel C200 (manufactured by Wako Pure Chemicals), eluent; hexane-ethyl acetate =20:1) to give 55.23 g of N-t-butoxycarbonyl-4-(4-fluorobenzylidene)piperidine as an oil, which was then crystallized by allowing to stand at room temperature overnight.

m.p. 69–70°C.

To 55.00 g of N-t-butoxycarbonyl-4-(4-fluorobenzylidene)piperidine was added 475 ml of an ice-cooled solution of 4 N hydrogen chloride in dioxane, followed by stirring at room temperature for 2 hours. The reaction solution was concentrated under reduced pressure, and the resulting crystals were recrystallized from isopropanol to give 40.72 g of 4-(4-fluorobenzylidene)piperidine hydrochloride.

m.p. 184–185.5° C.

The structures and physical property data of the present compound and the compounds prepared in the same manner as in Example 8 are shown in Table 2.

TABLE 1

Z—(CH₂)ₙ—N(piperidine)B¹—B²—Ar²·HX

| Comp. No. | Ex. No. | Z | n | B¹–B² | Ar² | HX | m.p. (° C.) (Solvent for recrystallization) |
|---|---|---|---|---|---|---|---|
| A-01*[1] | 4 | 5-(4-fluorophenyl)-4-methyl-1H-pyrazol-3-yl | 2 | C=CH | 4-fluorophenyl | — | 109.5–111.5 (IPE)*[3] |
| A-02*[1] | 4 | 5-(4-fluorophenyl)-4-methyl-1H-pyrazol-3-yl | 2 | C=CH | 3-fluorophenyl | (CO₂H)₂ | 136.5–138.0 (IPA)*[3] |
| A-03*[1] | 4 | 5-(4-fluorophenyl)-4-methyl-1H-pyrazol-3-yl | 2 | C=CH | 2-fluorophenyl | (CO₂H)₂ | 144.5–145.5 (IPA)*[3] |
| A-04*[1] | 4 | 4-methyl-5-(4-methylphenyl)-1H-pyrazol-3-yl | 2 | C=CH | 4-fluorophenyl | — | 119.0–120.0 (IPE)*[3] |
| A-05*[1] | 4 | 4-methyl-5-(4-methylphenyl)-1H-pyrazol-3-yl | 2 | C=CH | 4-fluorophenyl | (CO₂H)₂ | 128.5–129.5 (IPA)*[3] |
| A-06*[1] | 4 | 5-(4-fluorophenyl)-4-methyl-1H-pyrazol-3-yl | 2 | C=CH | 4-methylphenyl | (CO₂H)₂ | 137.5–138.5 (IPA)*[3] |
| A-07*[2] | 3 | 4-(4-fluorophenyl)-5-methyl-2-methylthio-1H-imidazol-1-yl | 2 | CH—C(O) | 4-fluorophenyl | — | 167.0–168.0 (Hex-EtOAc) |

TABLE 1-continued

Z—(CH2)n—N‾‾B¹—B²—Ar²·HX

| Comp. No. | Ex. No. | Z | n | B¹–B² | Ar² | HX | m.p. (° C.) (Solvent for recrystallization) |
|---|---|---|---|---|---|---|---|
| A-08*² | 3 | 2-(methylthio)-4-(4-fluorophenyl)-5-methyl-1H-imidazole | 2 | C=CH | 3-fluorophenyl | — | 123.5–124.5 (Hex-EtOAc) |
| A-09 | 3 | 4-(4-fluorophenyl)-2-hydroxy-5-methylthiazole | 2 | CH—C(O) | 4-fluorophenyl | — | 168.0–169.5 (Tol-EtOAc) |
| A-10 | 3 | 4-(4-fluorophenyl)-2-hydroxy-5-methylthiazole | 2 | C=CH | 3-fluorophenyl | — | 140.5–142.0 (Hex-EtOAc) |
| A-11 | 5 | 4-(4-methylphenyl)-5-methylpyrimidine | 2 | C=CH | 3-fluorophenyl | 2HCl | 143.5–145.5 (EtOH) |
| A-12 | 5 | 4-(4-methylphenyl)-5-methylpyrimidine | 2 | C=CH | 2-fluorophenyl | 2HCl | 144.5–146.5 (MeOH-IPE) |
| A-13 | 6 | 4-(4-fluorophenyl)-2-mercapto-5-methylpyrimidine | 2 | C=CH | 2-fluorophenyl | — | 157.0–158.0 (EtOAc) |
| A-14 | 7 | 4-(4-fluorophenyl)-2-(methylthio)-5-methylpyrimidine | 2 | C=CH | 2-fluorophenyl | 2HCl | Amorphous*⁴ |

TABLE 1-continued

Z—(CH$_2$)$_n$—N‌‌‌‌‌‌‌‌‌‌‌B$^1$—B$^2$—Ar$^2$·HX

| Comp. No. | Ex. No. | Z | n | B$^1$–B$^2$ | Ar$^2$ | HX | m.p. (° C.) (Solvent for recrystallization) |
|---|---|---|---|---|---|---|---|
| A-15 | 6 | (2-Me, 4-(4-F-phenyl)pyrimidin-5-yl, 5-Me) | 2 | C≡CH | 4-F-phenyl | — | Amorphous*5 |
| A-16 | 6 | (2-H$_2$N, 4-(4-F-phenyl)pyrimidin-5-yl, 5-Me) | 2 | C≡CH | 2-F-phenyl | — | Amorphous*6 |

In Table 1,
Comp. No.; Compound Number
Ex. No.; Example Number used for synthesis of the compound.
Solvent for recrystallization; IPE =diisopropyl ether, IPA=isopropyl alcohol, Hex=hexane, EtOAc=ethyl acetate, Tol=toluene, EtOH=ethanol, MeOH=methanol
*1: Only one of pyrazole tautomers is listed.
*2: only one of imidazole tautomers is listed.
*3: Solvent for crystallization
*4: Compound A-14
H$^1$-NMR (CDCl$_3$) δ(ppm); 2.54(3H, s), 2.52–3.61(12H, m), 5.55(1H, br. s), 6.40(1H, s), 7.15–7.43(6H, m), 7.63–7.78(2H, m), 8.70(1H, s), 11.18(1H, br. s)

MS m/e; 438 (M$^+$1,100%)
*5; Compound A-15
H$^1$-NMR (CDCl$_3$) δ(ppm); 2.30–2.51(10H, m), 2.75(3H, s), 2.84(2H, t, J=7.7), 6.22(1H, s), 6.94–7.23(6H, m), 7.48–7.58(2H, m), 8.60(1H, s)
MS m/e; 406 (M$^+$+1), 204 (100%)
*6; Compound A-16
H$^1$-NMR (CDCl$_3$) δ(ppm);
2.35–2.49(10H, m), 2.68–2.75(2H, m), 4.99(2H, br. s), 6.19(1H, s), 6.99–7.21(6H, m), 7.46–7.53(2H, m), 8.28(1H, s)
MS m/e; 407 (M$^+$+1), 204 (100%)

TABLE 2

HN-piperidin-4-ylidene-C(Ar)(R$^1$) ·HX

| Comp. No. | Ar$^2$ | R$^1$ | HX | m.p. (° C.) | Solvent for recrystallization |
|---|---|---|---|---|---|
| B-01 | 4-F-phenyl | H | HCl | 184.0–185.5 | IPA |
| B-02 | 3-F-phenyl | H | HCl | 199.0–200.5 | IPA |

TABLE 2-continued

Structure: HN-piperidine=C(Ar)(R¹)·HX

| Comp. No. | Ar² | R¹ | HX | m.p. (° C.) | Solvent for recrystallization |
|---|---|---|---|---|---|
| B-03 | 2-F-phenyl | H | HCl | 196.5–197.5 | IPA |
| B-04 | 4-Cl-phenyl | H | HCl | 207.0–208.0 | IPA |
| B-05 | 4-Br-phenyl | H | HCl | 207.0–208.5 | IPA |
| B-06 | 3,4-di-Cl-phenyl | H | HCl | 183.5–185.0 | IPA |
| B-07 | 4-Me-phenyl | H | HCl | 223.0–224.0 | IPA |
| B-08 | 3-CF₃-phenyl | H | HCl | 138.0–139.0 | IPA–IPE |
| B-09 | phenyl | H | HCl | 187.5–188.5 | IPA |
| B-10 | 4-OMe-phenyl | H | HCl | 178.5–179.5 | IPA |
| B-11 | 4-F-phenyl | H | HCl | 137.0–138.0 | IPA–IPE |

In Table 2,

Comp. No.; Compound Number

Solvent for recrystallization; IPA=isopropyl alcohol, IPE=diisopropyl ether.

Experiment [Receptor Binding Assay]

1. Dopamine $D_4$ Receptor Binding Assay

Chinese hamster ovarium (CHO) cell membranes wherein human $D_{4.2}$ receptor was expressed were used as a receptor preparation.

[³H]spiperone was used as [³H]-labeled ligand.

A binding reaction using the [³H]-labeled ligand was carried out according to the following method as described in Eur. J. Pharmacol., 233, 173(1993).

Dopamine $D_{4.2}$ Receptor Binding Assay: The CHO cell membranes wherein human $D_{4.2}$ receptor was expressed, [³H]spiperone (0.5 mM) and each test drug were reacted in 50 mM Tris-hydrochloric acid buffer (pH 7.4) containing 5 mM EDTA, 1.5 mM $CaCl_2$, 5 mM KCl and 120 mM NaCl at 27° C. for 2 hours.

After completion of the reaction, the reaction solution was filtered by suction through a glass filter (GF/B), and the radioactivity on the filter was measured by a liquid scintillation spectrometer.

The binding under the reaction in the presence of 10 μM haloperidol was defined as non-specific binding of [$^3$H] spiperone, and the difference between the total binding and the non-specific binding was defined as specific binding. An inhibition curve was obtained by reacting a definite concentration of [$^3$H]spiperone with various concentrations of test drug under the above-mentioned conditions, and the concentration (IC$_{50}$) of the test drug to exhibit 50% inhibition of [$^3$H]spiperone binding was determined by the inhibition curve. The results are shown in Table 3.

2. Dopamine D$_2$ Receptor Binding Assay

Rat striatum membrane was used as a receptor preparation.

[$^3$H]raclopride was used as [$^3$H]-labeled ligand.

A binding reaction using the [$^3$H]-labeled ligand was carried out according to the following method as described in Mol. J. Pharmacol., 43, 749(1993).

Preparation of Receptor Preparation: Rat striatum was homogenized in 50 mM Tris-hydrochloric acid buffer (pH 7.4), centrifuged at 48,000×g, and the precipitate was washed once with a Tris-hydrochloric acid buffer. The precipitate was suspended in 50 mM Tris-hydrochloric acid buffer (pH 7.4) containing 120 mM NaCl, 1.5 mM KCl, 2 mM CaCl$_2$ and 1 mM MgCl$_2$ to give a membrane preparation.

Dopamine D$_2$ Receptor Binding Assay: The membrane preparation (0.5 mg of protein/ml), [$^3$H]raclopride (1 nM) and each test drug were reacted at 25° C. for an hour.

After completion of the reaction, the reaction solution was filtered by suction through a glass filter (GF/B), and the radioactivity on the filter was determined by a liquid scintillation spectrometer.

The binding under the reaction in the presence of 10 μM haloperidol was defined as non-specific binding of [$^3$H] raclopride, and the difference between total binding and non-specific binding was defined as specific binding. An inhibition curve was obtained by reacting a definite concentration of [$^3$H]raclopride with varied concentrations of the test drug under the above-mentioned conditions, and the concentration (IC$_{50}$) of the test drug to exhibit 50% inhibition of [$^3$H]raclopride binding was determined by the inhibition curve. The results are shown in Table 3.

TABLE 3

| Compound No. | IC$_{50}$ (nM) D$_4$ | IC$_{50}$ (nM) D$_2$ |
|---|---|---|
| A-01 | 1.23 | 152.0 |
| A-02 | 1.12 | 32.0 |
| A-03 | 0.85 | 26.6 |
| A-04 | 1.96 | 55.9 |
| A-05 | 1.12 | 89.0 |
| A-06 | 2.85 | 170.7 |
| A-08 | 1.12 | 61.4 |
| A-09 | 2.85 | 107.2 |
| A-10 | 1.96 | 73.9 |
| A-11 | 4.53 | 521.4 |
| A-12 | 2.15 | 359.4 |
| A-13 | 1.35 | >1000 |
| A-14 | 12.6 | 147.7 |
| A-16 | 1.96 | 129.2 |

Industrial Applicability

The compounds of the present invention are useful for the prevention or the treatment of schizophrenia and problem behaviors associated with cerebrovascular diseases or senile dementia, and they are highly effective when administered orally, and are useful as drugs without extrapyramidal diseases as side-effects.

What is claimed is:

1. An aromaheterocyclic derivative represented by Formula [I]:

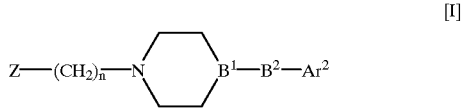

wherein Z is a group represented by the following Formula [II], [III], [IV] or [V]:

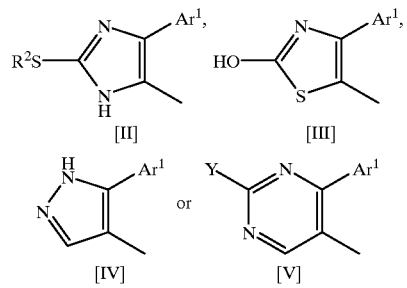

wherein Ar$^1$ is a phenyl group or a phenyl group substituted with a halogen atom or an alkyl group of 1 to 5 carbon atoms, R$^2$ is an alkyl group of 1 to 5 carbon atoms, Y is a hydrogen atom, a mercapto group, an alkylthio group of 1 to 5 carbon atoms, an amino group or an amino group substituted with one or two alkyl groups having 1 to 5 carbon atoms, Ar$^2$ is a phenyl group of one or two substituents selected from the group consisting of a halogen atom, an alkyl group of 1 to 5 carbon atoms, an alkoxy group of 1 to 5 carbon atoms, a hydroxyl group and a trifluoromethyl group, or a phenyl group, B$^1$–B$^2$ is CH—CO or C=C(R$^1$) (wherein R$^1$ is a hydrogen atom or an alkyl group of 1 to 5 carbon atoms), and n is an integer of 1 to 4; or a pharmaceutically acceptable salt thereof.

2. The aromaheterocyclic derivative according to claim 1 wherein Z is a group represented by Formula [II], Ar$^1$ is a fluorophenyl group, Ar$^2$ is a phenyl group substituted with a halogen atom, B$^1$–B$^2$ is CH—CO or C=CH and n is 2 in Formula [I]; or the pharmaceutically acceptable salt thereof.

3. The aromaheterocyclic derivative according to claim 1 wherein Z is a group represented by Formula [III], Ar$^1$ is a fluorophenyl group, Ar$^2$ is a phenyl group substituted with a halogen atom, B$^1$–B$^2$ is CH—CO or C=CH and n is 2 in Formula [I]; or the pharmaceutically acceptable salt thereof.

4. The aromaheterocyclic derivative according to claim 1 wherein Z is a group represented by Formula [IV], Ar$^1$ is a phenyl group or a phenyl group substituted with a fluorine atom or a methyl group, Ar$^2$ is a phenyl group substituted with a halogen atom or an alkyl group of 1 to 5 carbon atoms, B$^1$–B$^2$ is C=CH and n is 2 in Formula [I]; or the pharmaceutically acceptable salt thereof.

5. The aromaheterocyclic derivative according to claim 1 wherein Z is a group represented by Formula (V), Ar$^1$ is a fluorophenyl group, Ar$^2$ is a phenyl group substituted with a halogen atom, Y is a hydrogen atom, a mercapto group or a methylthio group, B$^1$–B$^2$ is CH—CO or C=CH and n is 2 in Formula [I]; or the pharmaceutically acceptable salt thereof.

6. A pharmaceutical composition comprising the aromaheterocyclic derivative according to claim 1 and a pharmaceutically acceptable carrier.

* * * * *